(12) United States Patent
Mihashi et al.

(10) Patent No.: US 7,971,753 B2
(45) Date of Patent: Jul. 5, 2011

(54) CONTAINER WITH A FILTER

(75) Inventors: Hirokazu Mihashi, Osaka (JP);
Yasuyuki Shiraishi, Osaka (JP);
Masaru Otsuka, Aichi (JP); Yorihisa Uetake, Aichi (JP)

(73) Assignees: Taisei Kako Co., Ltd., Osaka (JP);
Nihon Tenganyaku Kenkyusyo Co., Ltd., Aichi (JP)

( * ) Notice: Subject to any disclaimer, the term of this patent is extended or adjusted under 35 U.S.C. 154(b) by 841 days.

(21) Appl. No.: 10/578,916

(22) PCT Filed: Sep. 17, 2004

(86) PCT No.: PCT/JP2004/013631
§ 371 (c)(1),
(2), (4) Date: Aug. 7, 2006

(87) PCT Pub. No.: WO2005/044689
PCT Pub. Date: May 19, 2005

(65) Prior Publication Data
US 2007/0090044 A1    Apr. 26, 2007

(30) Foreign Application Priority Data
Nov. 11, 2003  (JP) .................................. 2003-381847

(51) Int. Cl.
*B01D 24/00*  (2006.01)
*A61J 1/14*   (2006.01)
*B65D 47/18*  (2006.01)
*B65D 83/28*  (2006.01)

(52) U.S. Cl. .......... 222/95; 222/105; 222/107; 222/109; 222/189.06; 222/189.08; 222/212; 222/215; 222/420

(58) Field of Classification Search ............... 222/92, 222/94, 95, 105, 107, 109, 111, 189.06, 189.08, 222/206, 209, 212, 215, 386.5, 420; 210/282, 210/321.89, 469
See application file for complete search history.

(56) References Cited

U.S. PATENT DOCUMENTS

| | | | |
|---|---|---|---|
| 2,715,980 A * | 8/1955 | Frick .............................. | 222/183 |
| 3,240,399 A * | 3/1966 | Frandeen ...................... | 222/211 |
| 4,020,978 A * | 5/1977 | Szczepanski ................. | 222/209 |
| 5,012,956 A * | 5/1991 | Stoody ............................ | 222/94 |
| 5,497,910 A * | 3/1996 | Meadows et al. ............... | 222/95 |
| 6,030,632 A * | 2/2000 | Sawan et al. .................. | 424/405 |
| 2002/0130139 A1* | 9/2002 | Shiraishi et al. ............. | 222/105 |
| 2002/0153386 A1* | 10/2002 | Uetake et al. ..................... | 222/1 |

FOREIGN PATENT DOCUMENTS

| | | |
|---|---|---|
| JP | 2711922 | 10/1998 |
| JP | 2002-80055 | 3/2002 |
| JP | 35-31876 | 5/2004 |
| WO | WO 90/04547 | 5/1990 |

* cited by examiner

*Primary Examiner* — Kenneth Bomberg
(74) *Attorney, Agent, or Firm* — Fisher, Christen & Sabol

(57) ABSTRACT

A filter-equipped container which, particularly in a small-sized eyedrop bottle or the like, is capable of accurate dropping while preventing bubbles from being involved when a contents liquid is to be delivered through a delivery port. To solve such problem, a plug body 12 disposed in the mouth of a bottle 10 is provided with a delivery passage for delivering contents liquid received in the bottle 10, the delivery passage being provided with a filter 25. The filter 25 is composed of a filter film 25a for filtering bacteria to prevent the latter from permeating from upstream to downstream as seen in the direction of delivery, and a contents liquid holding member 25b of porous material that has microscopic pores, disposed upstream of the filter film 25a, the contents liquid holding member 25b being in planar contact with the filter film 25a.

5 Claims, 6 Drawing Sheets

(a)

(b)

PRIOR ART

US 7,971,753 B2

CONTAINER WITH A FILTER

This application is a 371 national stage application of International Patent Application No. PCT/JP2004/013631, filed on Sep. 17, 2004, that has priority benefit of Japanese Patent Application No. 2003-381847, filed on Nov. 11, 2003.

FIELD OF THE INVENTION

The present invention relates to a discharging container with a filter, which is suitable for use as an aseptic eyedropper.

BACKGROUND ART

The FIG. 6 shows the commonly used bottle having a filter at its discharging opening, which stores water-soluble drug as internal liquid (U.S. Pat. No. 2,711,922). In these common bottles, most of the water-soluble drug is stored in the bottom of the bottle after usage, while a little of it stays clinging on the inside face side of a discharging opening 100.
Patent document 1: The Japanese Patent Gazette No. 2711922.

In suchlike state, when the bottle is put upside-down and squeezed to discharge the water-soluble drug, the water-soluble drug staying on the inside face of the discharging opening 100 may be discharged including air in the bottle, and the air may form air bubbles. If the air bubbles are formed around the discharging opening 100 in the described manner, the water-soluble drug spatters around when the air bubbles burst. Therefore, to drop the water-soluble drug with accuracy is difficult. Additionally, once a big air bubble is formed, a hydrophilic filter containing water becomes a barrier. Thus it is impossible to drop the water-soluble drug without generating the high pressure over the bubble point of the filter. Or the water-soluble drug goes along the surface of the air bubble to the downside surface of it before the air bubble bursts, so that it becomes instable since more than anticipated amount of the drug solution will be dropped or the like thing will happen. Aforementioned structural problem is a crucial defect for medical instruments since the things especially like eye drops which is instilled into patients' eyes by doctors are required to be dropped quickly and precisely in a precise amount.

SUMMARY OF THE INVENTION

Consequently, the object of the present invention is to provide a container with a filter, which is able to prevent air bubbles from sticking when liquid in the container is discharged through the discharging opening and to drop the liquid with precision.

In order to achieve the aforementioned object, the present invention has employed a technological feature as summarized below.

In other words, the present invention is a container with a filter comprising a bottle, a plug body placed on a mouth portion of the bottle and providing a discharging pass for discharging internal liquid kept in the bottle, and a filter provided in the discharging pass, wherein said filter has a filtration film to filter out bacteria for preventing bacteria from percolating from downstream side to upstream side in the direction of discharging and an internal liquid holding member which is made of porous substance and placed upstream side of the filtration film, and a surface of said internal liquid holding member is in contact with a surface of the filtration film.

As the liquid kept in the bottle, water-based drug product, wherein a variety of substances are dissolved or dispersed in the water as solvent or dispersion medium, can preferably be used. For example, it includes drug solution or quasi-drugs such as eye drop, skin toner, potable water, and the like.

The discharging pass is a channel, in which the internal liquid passes through from the inside of the bottle to the outside of the bottle when the liquid is discharged, and its structure and form may be anything.

The internal liquid holding member means the member which has an ability to hold the internal liquid and its form, structure, and materials may be anything. For example, it can be made of porous substance such as a sponge, a silicone pad, or the like. Preferably, its pore diameter is in the range between a few μm and a few hundreds μm and it does not prevent extrusion of the internal liquid. It is preferable to make this holding member to adhere the filtration film so that it is possible to keep the filtration film wet at all times.

According to the aforementioned present invention, after discharging the internal liquid through the discharging pass, portion of the internal liquid is held by the internal liquid holding member so that air bubbles are prevented from generating around the discharging pass when the internal liquid is discharged, thus it is possible to drop the internal liquid without fail.

In the container with a filter of the present invention, the filtration film may be a thin film which is made of a porous substance whose average pore diameter around a downstream side surface is between 0.1 μm and 0.5 μm and becomes larger or stays equal as it goes to upstream side. This average pore diameter can be set depending on the use or size of the container, physicality of the contents, or the like. For example, in the case of the container for the eye drop, whose internal liquid is the eye drop whose consistency is low and of which the whole size is relatively small, it is preferable to set it around the range between 0.1 μm and 0.3 μm. While in the case of the container for the cosmetics, in which the consistency of the internal liquid is relatively high and of which the whole size is relatively large, it may be set around the range between 0.4 μm and 0.5 μm.

Also the pressure necessary for the internal liquid to pass thorough said holding member from upstream side to downstream side is preferably lower than or equal to 12 hPa.

Additionally, it is preferable to set the pressure necessary for the liquid to pass through said holding member from upstream side to downstream side lower than filtration resistance of the filtration film. According to this, dischargability of the internal liquid is not blocked, since the whole filtration resistance of both the filtration film and the holding member is equal to the filtration resistance of only the filtration film, even after placing the internal liquid holding member. It is possible to set the filtration resistance between 10 hPa and 50 hPa or between 10 hPa and 20 hPa as well, and it is preferable to set this resistance as low as possible.

The bottle may have an external layer bottle which is deformable by squeezing and an internal layer bag which is peelable from the external layer bottle, and said liquid may be kept in the internal layer bag. It is possible to increase a pressure of air between the external layer bottle and the internal layer bag, and it is possible to place in a manner wherein the internal layer bag is pressed by the pressurized air so that the liquid in the internal layer bag passes through said internal liquid holding member and said filtration film. The internal layer bag may be formed to deflate easily accompanying the decrease of the internal liquid. If the filtration film is formed from the thin hydrophilic membrane, in the condition wherein it is wet, it is possible to shut out air by the filtration film. Thus it is possible to prevent ambient air from flowing into the internal layer bag. Therefore it is possible to form an aseptic eyedropper which does not require preservation agents.

Preferably the internal layer bag has memory which expands said internal layer bag and generates negative pressure in the internal layer so that a pressure difference between the negative pressure and the ambient pressure becomes higher than the filtration resistance thus liquid left downstream side of the filtration film is aspirated to upstream side of the filtration film. Hereby it is possible to prevent the liquid left downstream side of the filtration film from staying there and to prevent bacteria from growing in the left liquid.

Also, in the present invention, it is preferable that the body of the inner layer is made from synthetic resin, the average thickness of the body is over 0.1 mm, more preferably, over 0.35 mm, and the average thickness of the body is less than 0.5 mm, more preferably, less than 0.4 mm. By that, the inner layer can be formed to have a desired elastic-memory.

Additionally, in the present invention, it is preferable to employ the composition in which the outer layer has an entry opening to bring the outside air in the room between the outer layer and the inner layer. By that, when pushing of the bottle is released, the ambient air flows in through the entry opening and the pressure between the outer layer and the inner layer becomes the ambient pressure, so that the difference of the pressure between the upper stream of the filter and the lower stream of the filter caused by the elastic-memory of the inner layer can be in the desired range without fail. It is possible to provide the distribution valve for the entry opening, but it is also possible to form the entry opening with an opening which is closed when the body of the bottle is pushed.

According to the present invention, especially in eyedroppers and the like, it is possible to prevent air bubbles from being generated around the discharging pass so that internal liquid is dropped smoothly and precisely.

THE PREFERRED EMBODIMENTS

With reference to the attached drawings, the present invention will hereinafter be described by way of an embodiment thereof.

Figure 1:
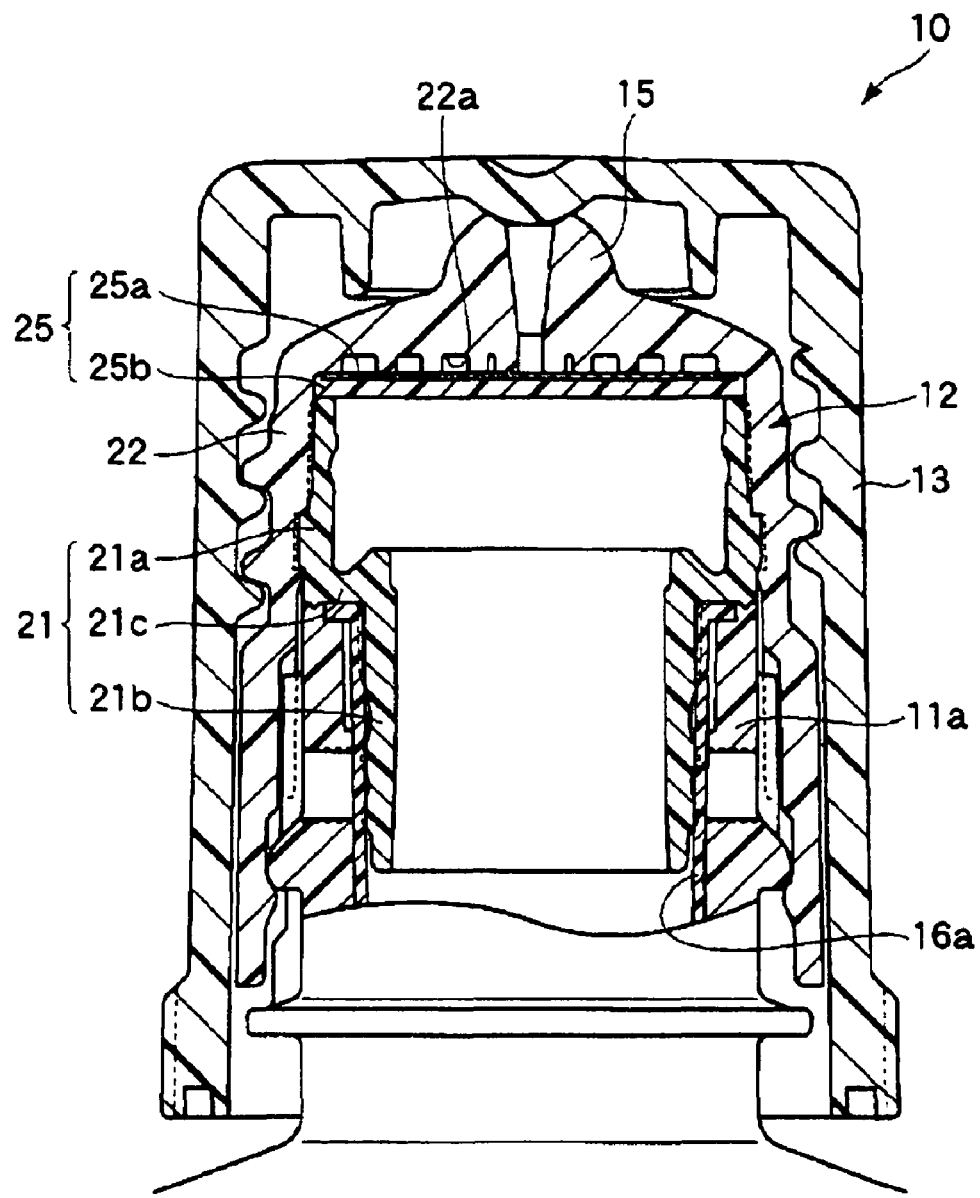
FIG. 1 is scale-up longitudinal sectional view of the relevant part of the eyedropper with a laminated film-peeling bottle of an embodiment of the present invention.
Figure 2:
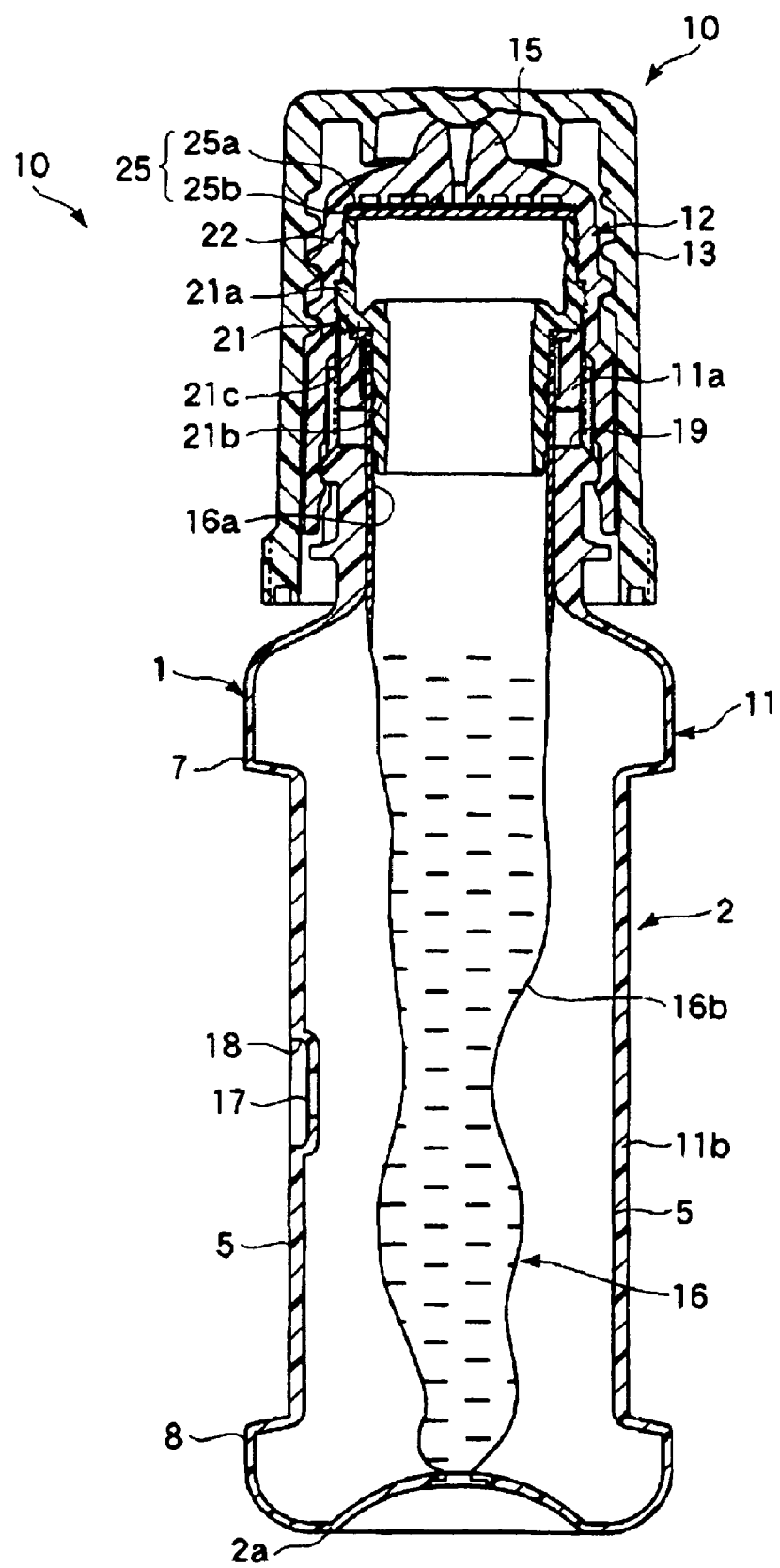
FIG. 2 is whole longitudinal sectional view of said eyedropper.

FIGS. 1 and 2 illustrate an eyedropper as a laminated bottle with an outer layer and an inner layer according to an embodiment of the present invention. This eyedropper 10 has a laminated film-peeling double layered bottle 11, which is produced by blow molding from a laminated parison having a bottom and composed of the inner layer and the outer layer, a plug body 12, which is fixed on a mouth portion 11a of the bottle 11, and a protection cap 13. It is formed in a manner wherein eye drops (fluids) are dropped from a point nozzle part 15 through a discharging pass inside of the plug body 12, when a user detaches the cap 13, makes the laminated bottle 11 upside down, and squeezes the body portion 11b by pushing, as shown in the FIG. 2.

Said laminated bottle 11 has a laminated structure composed of an external layer bottle 1 (squeezing bottle) which composes the outer layer and an internal layer bag 16 (fluids storing bag) which composes the inner layer. In the aftermath of blow molding, both the external layer bottle 1 and the internal layer bag 16 have a cylindrical mouth portion and a flat body portion in the cross sectional view. The external layer bottle 1 may be molded from, for example, PET, and PC or like synthetic resin, and the inner layer 16 may be molded from synthetic resin (e.g. polyolefin such as polyethylene) which has a property, in which it easily peels from the outer layer. Additionally, the mouth portion of the bag 16 forms an opening for discharging liquid.

Figure 3:
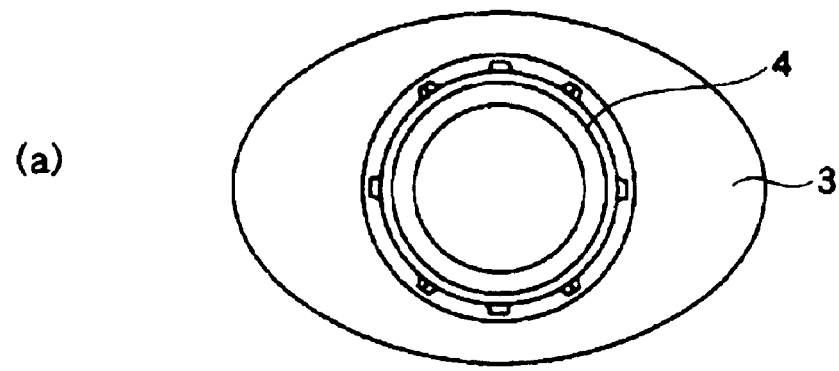
FIG. 3 is whole picture of the laminated film-peeling bottle of said eyedropper, which (a) is a plane view and (b) is an elevated view.
Figure 3:
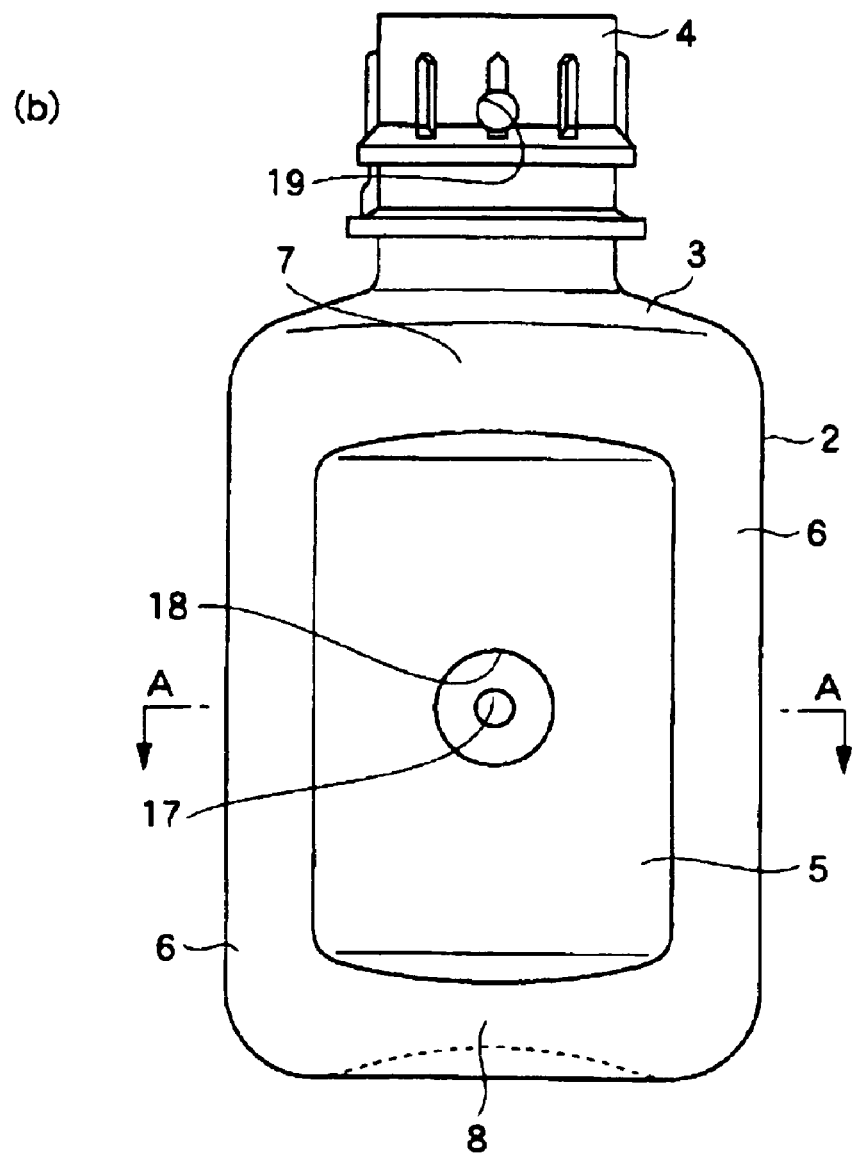
Figure 4:
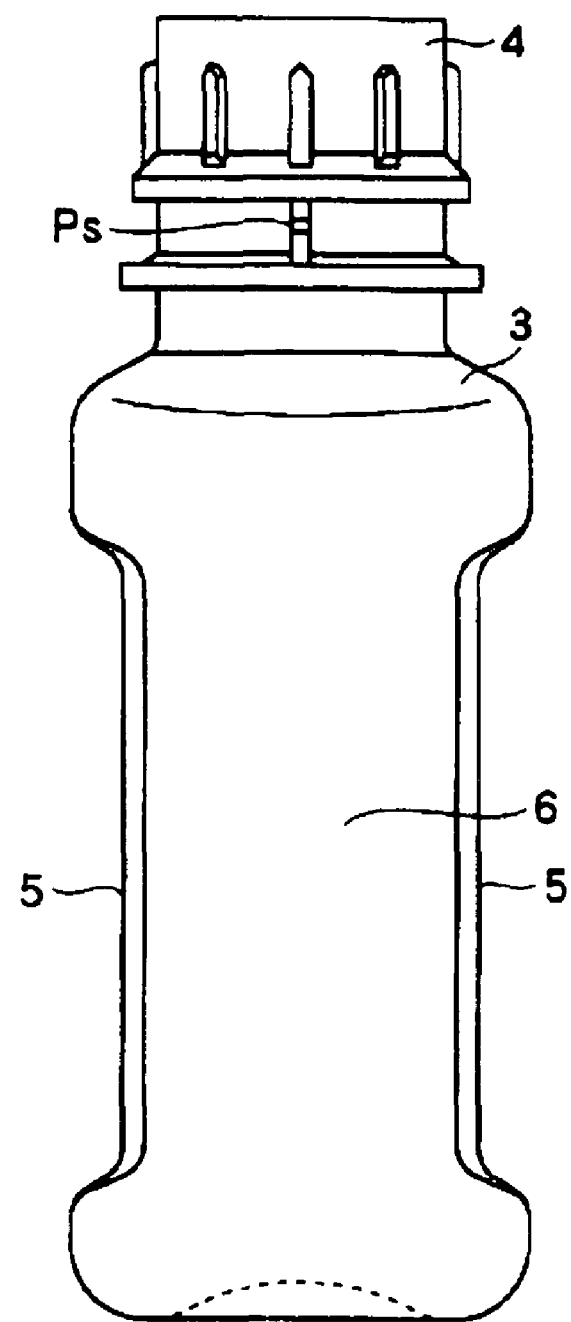
FIG. 4 is lateral view of said laminating film-peeling bottle.
Figure 5:
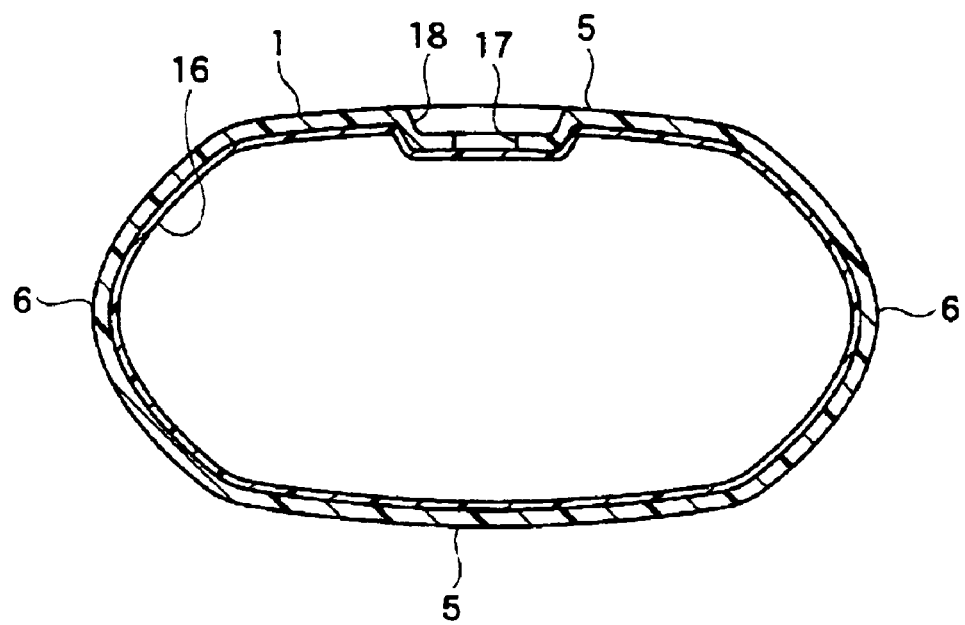
FIG. 5 is cross sectional view taken along the plane A-A of FIG. 3.
Figure 6:
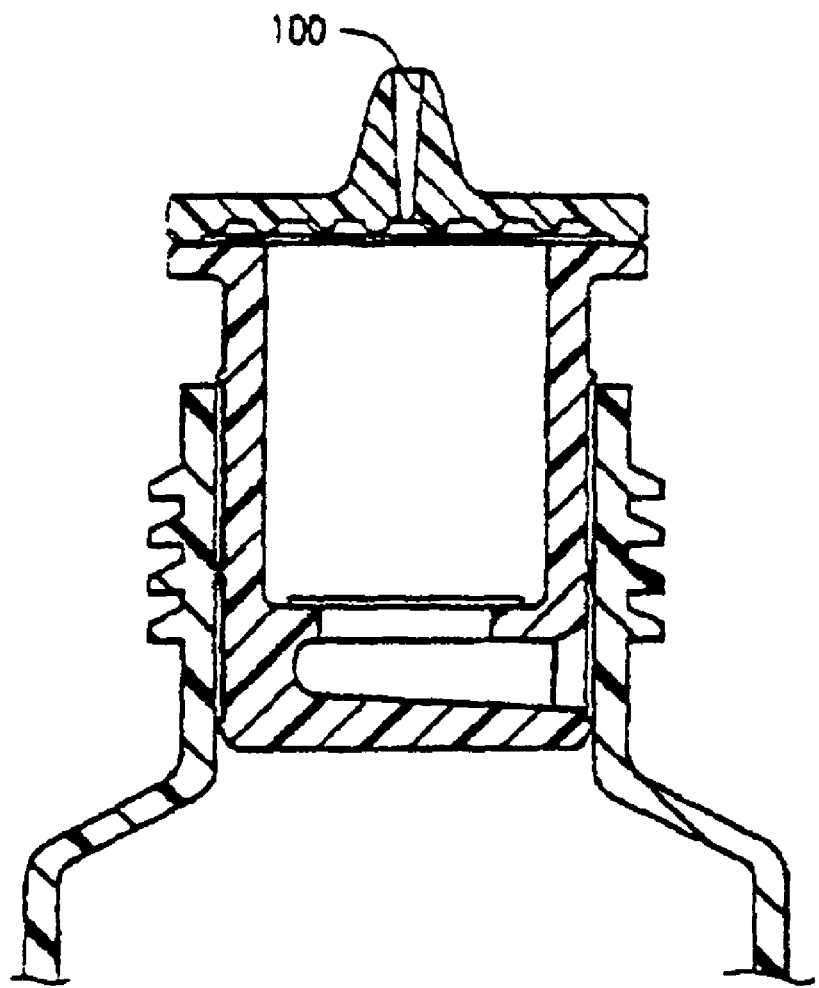
FIG. 6 is cross sectional view of the prior container with filter.

As shown in FIG. 3 to 5, the outer bottle 1 is formed in a manner wherein a cylindrical mouth portion 4 is provided at an upper end of a body portion 2, which is resiliently squeezable and formed in a cylindrical shape with a bottom, through a shoulder portion 3 whose diameter is getting smaller as it goes upwards. A peripheral wall of the body portion 2 is constituted in a shape of a long flat circle, in which the before-and-behind width is smaller than the right-and-left width of the body portion 2, from a pair of before and behind rigid wall parts 5 which face each other having a specified distance, and right and left flexible connecting wall parts 6 which connect either side of edge parts of these rigid wall parts 5. Each rigid wall part 5 (before-and-behind wall parts) has a rectangular shape of which the long side is in an up-and-down direction in a front view, and almost flat in a cross-section and a vertical-section. However, it may be unnecessary to be perfectly flat and it may be slightly curved. Each flexible connecting wall part 6 (right-and-left wall parts) has an arc shape in which longitudinal center portion projects outwardly in right-and-left direction, and its curvature radius is smaller than the minor axis of the body portion 2. Additionally, an upper end portion of each rigid wall part 5 is connected to the shoulder portion 3 through an upper flexible connecting part 7, and a lower end of each rigid wall part 5 is connected to a bottom portion 2a of the body 2 through a lower flexible connecting part 8. Therefore, a periphery of each rigid wall part 5 is surrounded only by said flexible parts 6, 7, and 8. Also before and behind rigid wall parts 5, the bottom portion 2a, and the shoulder portion 3 are connected integrally only by flexible parts 6, 7, and 8.

The upper flexible connecting part 7 and the lower flexible connecting part 8 are located more outwardly than the rigid wall part 5 in the direction of before-and-behind. Therefore, when the bottle 1 is blow-molded from said plastic parison, the elongation rate of the plastic becomes larger and each connecting part 7 and 8 is formed relatively thin-walled, so that the easily deformable flexibility is applied to these connecting parts 7 and 8. While the rigid wall part 5 is formed thick-walled, so that the difficult-to-deform rigidity is applied to the wall part 5. It is preferable to set average wall thickness of these connecting parts 7 and 8 to be thinner than half of the average wall thickness of the rigid wall part 5.

Also, horizontal width of the body 2 of the squeeze bottle 1 is 1.5 times larger than the longitudinal width (i.e. the distance between the outside surface of the before and behind rigid wall parts 5), at the time of the blow molding, and the elongation rate of the plastic at the portion which forms right and left flexible connecting wall parts 6, so that the average wall thickness of right and left flexible connecting wall parts 6 is thinner than the average wall thickness of the rigid wall part 5. Further, at the stage of the parison for a blow molding, it is possible to make the thickness of the portion which forms the rigid wall part 5 thicker than the thickness of the portion which forms the flexible connecting part.

Since the external layer bottle 1 is formed in the aforementioned manner, when the before and behind rigid wall parts 5 are made close to each other till the distance between the center portion of the top-to-bottom direction of the before and behind rigid wall parts 5 becomes half by pressing the center portion with two fingers, the right and left connecting parts 6 and the upper and lower connecting parts 7 and 8 are deformed in their elastic region in a manner wherein the upper and lower edges of the rigid wall parts 5 move following the said center.

In addition, an entry opening 17 for leading ambient air to the room between the body portion of the bottle 2 and a body 16a of the internal layer bag 16 is bored at the center portion of the both top-to-bottom and right-to-left direction of the front side of the rigid wall part 5 (front wall part) of the external layer bottle 1 of this embodiment. This entry opening 17 is formed from the opening going through the external layer bottle 1 from the inside to the outside, and not bored on the internal layer bag 16. Additionally, a circular formed concave part 18 whose diameter is larger than the one of the entry opening 17 is formed on the center portion of the both top-to-bottom and right-to-left of the rigid wall part 5. This concave part 18 is formed in a manner wherein it is caved in the bottle, and the diameter of which is approximately 5 mm. Aforementioned entry opening 17 is formed in the concave part 18. The entry opening 17 may be blocked by blocking the concave part 18 with a finger. The entry opening 17 doesn't have a check valve and constantly remains open, and the dimensions of this opening are approximately between 1 mm$^2$ and 2 mm$^2$.

Also an examination opening 19 which communicates with the entry opening 17 through the room between the external layer bottle 1 and the internal layer bag 16 is bored on a midway portion of the top-to-bottom direction of a mouth portion 4. In the present embodiment, two examination openings 19 are formed at the positions facing each other in the direction of the diameter. This examination opening 19 is also going through the external layer bottle 1 from the inside to the outside, and not bored on the internal layer bag 16. This examination opening 19 is blocked up with a mouth 16a of the internal layer bag 16 from inside, so that air between the outer layer 1 and the inner layer 16 is prevented from going out from the examination opening 19 during use of the eyedropper 10. To ensure this blocking by the internal layer bag 16, in the present embodiment, the mouth 16a of the internal layer bag 16 is pressed to the examination opening 19 by the aftermentioned inside plug 21. Thus, the examination opening 19 is blocked up with the internal layer bag 16 and the inside plug 21.

The mouth 16a of the internal layer bag 16 is pressed to the examination opening 19 by the inside plug 21, contacts to the opening portion 4 of the external layer bottle, and may have the elastic-memory.

Also, the body 16b of the internal layer bag 16, depending on the plastic materials used, for example, may have approximately 0.35 to 0.4 mm average thickness. It easily shrinks as the liquid inside decreases, however it also has a certain degree of elastic-memory toward the direction of expanding. This elastic-memory of the body 16b of the internal layer bag 16 is set out in a manner wherein the difference between the pressure in the internal layer bag 16 and the ambient pressure is to be between 40 hPa and 60 hPa. Also the elastic-memory of the body 16b is set out to be greater than the filtration resistance of the after-mentioned filter. Also, the body 16b of the internal layer bag 16 has the elastic-memory wherein the body 16b is easily deformed under the pressure between 400 hPa and 600 hPa, which affects during the step of the dropping by squeezing.

Additionally, the center of a bottom portion of the bag 16 is fixed to the center of the bottom portion of the external layer bottle 1, so that the bottom portion of the bag 16 is prevented from being lifted.

Aforementioned plug body 12 mainly includes an inside plug 21 fitted in the bottle mouth portion 4 and a nozzle cap 22 axially connected to the inside plug 21 and fitted around the periphery of bottle mouth portion 4.

The inside plug 21 is such, in which a first cylindrical portion 21a with its proximal end abutting against a distal end surface of the bottle mouth portion 4, a flange 21c which is placed inwardly in the direction of the diameter on the abutting point of said first cylindrical portion 21a and the bottle mouth portion 4, and a second cylindrical portion which extends from inside of this flange 21c to upstream side, are formed as a single piece. The second cylindrical portion 21b is fitted in the bottle mouth portion 4 air tightly and fluid tightly. Particularly in the present embodiment, the second cylindrical portion 21b extends toward lower (upstream side) than the examination opening 19, and aforementioned examination opening 19 is blocked from inside air tightly with this second cylindrical portion 21b.

The nozzle cap 22 is a generally cylindrical member, which includes a top plate provided with the nozzle portion 15 at its axially distal end, and they are formed as a single piece. The first cylindrical portion 21a of the inside plug 21 is fitted in the inner peripheral wall of the nozzle cap 22. An end periphery of the nozzle cap 22 has a smaller diameter cylindrical portion provided in a distal outer peripheral portion thereof with a step. The protection cap 13 is threadingly fitted around the periphery of the smaller diameter cylindrical portion.

A filter 25 is provided in a lower surface of the top plate of the nozzle cap 22. This filter 25 comprises a filtration film 25a and an internal liquid holding member 25b provided in the primary side (upstream side) of the filtration film 25a. Examples of the filtration film 25a include a hydrophilic porous planar film, a membrane filter, a sintered filter and a hydrophobic porous planar film, all of which are capable of preventing passage of bacteria (including pathogenic bacteria) from a downstream side (outside) to an upstream side (inside) of the filter 25. As this filtration film 25a, like such whose average diameter of the bore is between 0.1 μm and 0.3 μm are preferably adopted. More preferably, as the filtration film 25a, "MILLIPORE EXPRESS® PLUS membrane filter" manufactured by Millipore Co. is adopted. This filter is like such of which the diameters of pores of the primary side and the second side are different. The average diameter of pores around a surface of the second side is approximately 0.22 μm and the diameter of pores becomes larger as it goes to the primary side. As just described, by using the filter wherein the diameter of pores around the surface of the second side is as small as just to be able to filtrate bacteria and becomes larger as it goes to the primary side as a filtration film 25a, it is able to both keep the aseptic condition of the inner layer and make filtering resistance of the filtration film smaller.

An internal liquid holding member 25b is made in a discotic shape or a cylindrical shape from a silicone pad or the like and the microscopic pores (the diameter of which is from 10 μm to 0.1 mm) on it are able to hold the liquid in the container. Additionally, a rim of this internal liquid holding member 25b may or may not abut on the end of the first cylindrical portion 21a of the inside plug 21. This holding member 25b is, for example, formed by punching out the foamed sheet, whose thickness is from 0.7 mm to 3 mm, and which is made from nucleophile, whose average grain diameter is between 160 μm to 340 μm. The necessary pressure (infiltrate timing pressure) for the internal liquid to pass through the holding member 25b from the discharging upstream side (inside of the bottle) to the discharging downstream side (nozzle side) is preferable to be approximately between 4 hPa and 12 hPa.

The filtration resistance of the filtration film 25a is preferably approximately between 10 hPa and 50 hPa and higher than said infiltrate timing pressure of the holding member 25b. The resistance of the filtration film 25a is designed to be lower than the difference between a negative pressure in the inner room, which is caused by the elastic-memory of the body 16a of the internal layer bag 16 and the ambient pressure. This design is available by, specifically, molding multiples of laminated film-peeling bottles which differ from each other in their inner layer body thickness, carrying out the examination, and selecting the most preferable thickness which is agreeable to the shape and size of the plastic and the bottle used. Also, the filter 25 (in the present embodiment, the whole of the filtration film and internal liquid holding member) is provided in a manner wherein the pressure for vacuuming the air from the lower side is between 689 hPa and 4826 hPa, and the resistance is higher than the difference between the inner pressure of the inner bag 16 caused by the elastic memory of the body 16b of the inner bag 16, and the ambient air pressure. Additionally, the difference between the inner pressure of the internal layer bag 16, caused by the elastic memory of the inner layer and the ambient pressure, is smaller than the one at the bubble point of the filter 25 (and the filtration film 25a). The filtration resistance of the whole filter 25 is to be almost the same as the filtration film 25a by setting the infiltrate timing pressure of the holding member 25b lower than the filtration resistance of the filtration film 25a.

In addition, a communicating channel 22a which communicates with the nozzle part 15 is provided on the lower surface of the top plate of the nozzle cap 22. The internal liquid flowing through the filter 22 is provided to the nozzle part 15 through the communicating channel 22a. This communicating channel 22a comprises a first channel which radiates outwardly from the nozzle part 15 in the basal plane view, and multiples of circular second channels whose center is the nozzle part 15.

To discharge internal liquid from the nozzle part 15 using said eyedropper 10, as shown in FIG. 2, squeeze the body portion 2 of the external layer bottle 1 by pushing in a manner wherein the entry opening 17 is closed by a finger, so that the air between the internal layer 16 and the external layer 1 is pressurized and the internal layer bag 16 is compressed. In this manner, by generating inner pressure in the internal layer bag 16, the internal liquid is dropped from the nozzle 15 through the filter 25. After stopping pressing the bottle 11, leaving the finger from the entry opening 17 lets in the ambient air between the inner and outer layer 1 and 16 thorough the entry opening 17. After that, the liquid staying inside of a pass in the nozzle (i.e. a discharging pass end opening) is vacuumed to the upstream side of the filtration film 25a by the elastic-memory of the internal layer bag 16. In addition, the internal liquid is sheltered from the ambient air by the filtration film 25. In this case, if the filtration film 25a of the filter 25 is composed of a hydrophilic filter, it is possible to prevent the ambient air from entering into the inner layer since the ambient air cannot pass through the filter 25.

Then after dripping the internal liquid once, it becomes possible to prevent generating air bubbles around the discharging pass and to keep the filtration film 25a wet for a long time, since the internal liquid is hold in the holding member 25b.

The present invention is never limited to the conformations shown in the illustrated embodiment, but may be modified in any appropriate manner or fashion, within the realm of the technical ideas included in the claims.

What is claimed is:

1. A container with a filter comprising:
    a bottle having a mouth portion;
    a plug body placed on the mouth portion and providing a discharging pass for discharging internal liquid kept in the bottle;
    a filter provided in the discharging pass;
    said filter has a filtration film constructed to filter out bacteria for preventing bacterial from percolating from downstream side to upstream side in a direction opposite of discharging, and an internal liquid holding member which is made of porous substance having microscopic pores that hold the liquid therein in order to keep said film wet, and which is placed on upstream side of the filtration film;
    a surface of said internal liquid holding member is in contact with a surface of the filtration film; and
    said bottle comprises an external layer which is deformable by squeezing and an internal layer bag which is peelable from the external layer bottle, and said liquid is kept in the internal layer bag;
    the internal layer bag has memory which expands said internal layer bag and generates negative pressure in the interial layer bag so that a pressure difference between the negative pressure and the ambient pressure becomes higher than the filtration resistance, and the negative pressure aspirates liquid that remains in downstream side of the filtration film to upstream side of the filtration film.

2. The container with a filter as set forth in claim 1, wherein said filtration film is a thin film which is made of a porous substance whose average pore diameter around a downstream side surface is between 0.1 μm and 0.5 μM and becomes larger or stays equal as it goes to upstream side.

3. The container with a filter as set forth in claim 1, wherein a pressure necessary for the internal liquid to pass through said holding member from upstream side to downstream side is lower than or equal to 12 hPa.

4. The container with a filter as set forth in claim 1, wherein a pressure necessary for the internal liquid to pass through said holding member from upstream side to downstream side is lower than filtration resistance of the filtration film.

5. The container with a filter as set forth in claim 1, wherein said filtration film has a hydrophilicity.

* * * * *